United States Patent [19]

Sullivan et al.

[11] Patent Number: 6,060,084
[45] Date of Patent: May 9, 2000

[54] METHOD FOR PREPARING A CORE MATERIAL CONTAINMENT SYSTEM AND THE CORE MATERIAL CONTAINMENT SYSTEM PREPARED THEREBY

[75] Inventors: Radmila Sullivan, Dayton; Marvin L. Kidd, Beavercreek; Patrick Alan Lafferty, Tipp City, all of Ohio

[73] Assignee: Cannon Chemical Company, Dayton, Ohio

[21] Appl. No.: 09/141,188

[22] Filed: Aug. 27, 1998

Related U.S. Application Data

[60] Provisional application No. 60/057,732, Aug. 28, 1997.

[51] Int. Cl.[7] ............................. A61K 9/66; A61K 9/48; A61K 9/64
[52] U.S. Cl. .................... 424/455; 424/456; 424/451; 514/962; 428/40.2; 428/40.5; 427/213.3; 427/212; 264/4
[58] Field of Search ..................... 424/451, 462, 424/408, 452, 456; 428/40.2, 40.5; 427/213.3, 212; 264/4; 514/962

[56] References Cited

U.S. PATENT DOCUMENTS

| | | |
|---|---|---|
| 3,016,308 | 1/1962 | Macaulay . |
| 3,041,289 | 6/1962 | Katchen et al. . |
| 3,069,370 | 12/1962 | Jensen et al. . |
| 3,161,602 | 12/1964 | Herbig et al. . |
| 3,826,670 | 7/1974 | Rees ........................................ 106/308 |
| 3,839,064 | 10/1974 | Vincent .................................. 106/308 |
| 3,914,405 | 10/1975 | Shepherd et al. ......................... 424/49 |
| 3,922,354 | 11/1975 | Galluzzi et al. .......................... 426/96 |
| 3,929,988 | 12/1975 | Barth ........................................ 424/54 |
| 3,943,063 | 3/1976 | Morishita et al. ....................... 252/316 |
| 3,949,094 | 4/1976 | Johnson et al. ........................... 426/99 |
| 4,071,614 | 1/1978 | Grimm, III ............................... 424/49 |
| 4,173,492 | 11/1979 | Pollard .................................... 106/308 |
| 4,202,878 | 5/1980 | Ritze et al. . |
| 4,348,378 | 9/1982 | Kosti ........................................ 424/7 |
| 4,376,762 | 3/1983 | Hauschild et al. ....................... 424/49 |
| 4,376,763 | 3/1983 | Barth et al. ............................... 424/49 |
| 4,459,277 | 7/1984 | Kosti ...................................... 424/7.1 |
| 4,525,342 | 6/1985 | Weiss et al. .............................. 424/49 |
| 4,582,701 | 4/1986 | Piechota, Jr. ............................. 424/52 |
| 4,647,451 | 3/1987 | Piechota, Jr. ............................. 424/52 |
| 4,814,160 | 3/1989 | Carter et al. ............................ 424/7.1 |
| 4,978,483 | 12/1990 | Redding, Jr. ........................... 264/4.32 |
| 4,978,521 | 12/1990 | Blue ....................................... 424/7.1 |
| 4,980,154 | 12/1990 | Gordon .................................... 424/53 |
| 5,037,485 | 8/1991 | Chromecek et al. ....................... 134/7 |
| 5,104,763 | 4/1992 | Ong et al. ............................... 430/109 |
| 5,209,879 | 5/1993 | Redding, Jr. ............................. 264/23 |
| 5,271,881 | 12/1993 | Redding, Jr. ............................ 264/432 |
| 5,460,756 | 10/1995 | Redding, Jr. .............................. 264/4 |
| 5,556,583 | 9/1996 | Tashiro et al. ........................... 264/4.1 |
| 5,589,194 | 12/1996 | Tsuei et al. ............................. 424/497 |
| 5,637,389 | 6/1997 | Colvin et al. ......................... 428/368.4 |
| 5,718,921 | 2/1998 | Mathiowitz et al. .................... 424/497 |
| 5,741,591 | 4/1998 | Tashiro et al. ....................... 428/402.24 |
| 5,741,592 | 4/1998 | Lewis ................................. 428/402.24 |
| 5,756,073 | 5/1998 | Miller et al. ............................. 424/49 |
| 5,766,637 | 6/1998 | Shine et al. ............................ 424/497 |

*Primary Examiner*—Thurman K. Page
*Assistant Examiner*—Brian K. Seidleck
*Attorney, Agent, or Firm*—Thompson Hine & Flory LLP

[57] ABSTRACT

A method for preparing a core material containment system which prevents or controls leaching of the core material from the containment system, said method comprising the steps of: (1) providing a shell material having a softening temperature above about 70° F.; (2) heating said shell material to a temperature at or above the softening temperature of said shell material; (3) adding an oil to the molten shell material, said oil being compatible with said shell material but not a solvent for the shell material in a solid state; (4) uniformly dispersing a core material in the molten, oil-containing shell material; (5) subdividing said molten, oil-containing shell material having said core material dispersed therein into individual droplets of a predetermined size; (6) cooling the molten, oil-containing shell material having said core material dispersed therein to a temperature below its softening temperature to obtain a plurality of encapsulated or coated particles of said core material; and (7) recovering said particles of encapsulated or coated core material; and a core material containment system prepared by such method are described.

22 Claims, No Drawings

METHOD FOR PREPARING A CORE MATERIAL CONTAINMENT SYSTEM AND THE CORE MATERIAL CONTAINMENT SYSTEM PREPARED THEREBY

CROSS-REFERENCE TO RELATED APPLICATION(S)

The present application claims priority under 35 U.S.C. §119 from U.S. Provisional Patent Application Serial No. 60/057,732 filed Aug. 28, 1997; the disclosure of which is incorporated herein by reference.

BACKGROUND OF THE INVENTION

The present invention related to a core material containment system which prevents or controls leaching of the core material from the containment system, and more specifically to a core material coated or encapsulated with a containment system comprising an organic material such as a wax or gelling agent, and an oil such as a mineral oil.

Color has been acknowledged to play an important role in consumer acceptance of many products. In many cases color has been used to distinguish particular products in the market place and to identify products having particular distinct properties. Colored products, particularly food products and other human consumable products such as toothpaste are usually formulated by merely adding the desired dye to the other components prior to the mixing stage of the process. As the dyes currently utilized in toothpaste are all water-soluble, and large amounts of water are present in toothpaste, the desired color spreads and uniformly colors the entire product. As an alternative to uniformly dispersing colored particles throughout the product, colored particles have been effectively concentrated into well defined areas of the product while other areas contain no colored particles creating a product having alternating stripes of color and a contrasting color.

U.S. Pat. No. 4,202,878 to Ritze describes a toothpaste product having numerous, discrete, well-defined centers of contrasting color or colors randomly but uniformly distributed therethrough which presents a striking and highly distinctive appearance. The main requirements of the pigmented particles in producing the speckled product is that the particles must be water-insoluble, that they be of sufficient size to be discernible so as to maintain particle integrity and distinctness in the toothpaste base until the product is used; and that the particles not leach, i.e., bleed, and color the entire dentifrice. Since the dyes and pigments certified for use in dentifrice products by the U.S. Food and Drug Administration (FDA) contain water-soluble components and toothpastes generally contain sufficient quantities of water to cause the dyes to leach and color the entire product, it has not been possible to prepare speckles which are colorfast and yet are of a sufficiently small particle size so that they are not detectable in the mouth. Solid water-insoluble pigment particles of the size required to produce the speckled effect generally produce an unpleasant gritty "berry seed" sensation in use, and actually become lodged between the teeth unless they break up into small particles when brushed upon the teeth.

SUMMARY OF THE INVENTION

In accordance with the present invention, a core material such as a solid particle; a semi-solid, e.g., a gel; or a liquid is coated or encapsulated or otherwise contained in a core containment system which prevents or controls leaching or bleeding of the core material from the containment system.

It is thus an object of the present invention to provide a method for preparing a core containment system.

This and other objects are accomplished in accordance with a method for preparing the non-leachable core containment system which comprises the following steps:

(1) providing a shell material having a softening temperature above about 70° F.;

(2) heating said shell material to a temperature at or above the softening temperature of said shell material;

(3) adding an oil to the molten shell material, said oil being compatible with said shell material, but not a solvent for the shell material in a solid state;

(4) uniformly dispersing a core material in said molten, oil-containing shell material;

(5) subdividing said molten, oil-containing shell material having said core material dispersed therein into individual droplets of a predetermined size;

(6) cooling the molten, oil-containing shell material having said core material dispersed therein to a temperature below its softening temperature to obtain a plurality of encapsulated or coated particles of said core material; and (7) recovering said particles of encapsulated or coated core material.

DETAILED DESCRIPTION OF THE INVENTION

The core containment system of the present invention is useful in a wide variety of applications where encapsulated core materials can be beneficially employed and is particularly useful in products designed for human consumption, e.g., in toothpaste, chewing gum and as food coloring such as used in cakes and other bakery products where it is desirable that the pigment particles provide a specific appearance without the color from the core material leaching or bleeding into an area which does not contain such core material. Typically, the core material of such containment systems are essentially color-fast and, in the case of food products, non-toxic. The color of the pigment particles should be readily distinguishable from that of the shell material and the product into which the contained core material is incorporated. For example, the color of the toothpaste is white; therefore, the color of the pigment may be of a distinctly different color, such as blue, green, red, etc. when used in the production of toothpaste. If the product or shell material is colored, the pigment could be white as well as another color.

The core material should not readily leach a significant amount of color in the presence of water. Thus, the core material containment system of the present invention should be effective to prevent or control the leaching or bleeding of the core material from the system. When used in the preparation of food products, the core material must be FDA approved or on the Generally Recognized As Safe (GRAS) list of safe products for human consumption. In a preferred aspect of the invention, water-soluble dyes which are approved for drug and cosmetic use (D&C) or for food, drug and cosmetic use (FD&C) such as dye lakes prepared by extending calcium or aluminum salts of FD&C water-soluble dyes on alumina, such as aluminum lake D&C blue #1, D&C Red #'s 2, 3, 6, 7, 8, 9, 10, 11, 12, 13, 19, 30, 31, 36 and 37 lakes, FD&C Green #1 lake, FD&C Blue #'s 1 and 2 lakes, FD&C Yellow #5 lake, and FD&C Red #'s 1 and 2 lakes are used as the core material of the present invention. Also useful core materials are dyed synthetic resin particles;

natural vegetable colors like annatto, paprika, carotenoids, etc.; freeze dried particles or spray dried particles; and, optionally, natural or synthetic dyed and/or flavored crystals. However, other core materials which can be used in the present invention include, for example, inorganic pigments such as titanium dioxide, zinc oxide, chromium oxide greens, carbon blacks, ultramarine blues and pinks, and ferric oxides; and dyed cellulose particles such as dyed cotton linters, dyed wood pulp; and liquid coloring agents such as dyes.

The amount of core material employed in the present invention depends to a large extent on the particle size where solid pigment particles are used. For example, a given weight of small particles has a greater surface area than the same weight of larger particles, thus lesser amounts of small particles are required to produce the same effect as given amounts of large particles. The core material typically comprises less than about 3% by weight of the containment system. Preferably, the core material is used at a concentration of about 0.3 to 3% by weight of the containment system. A core material containment system having a core material concentration of about 1.5% to 2.0% has been found to be effective for most applications.

The mean particle size of the finished particles should be fairly consistent for each application but, depending upon the particular use, can vary over a wide range, e.g., up to 500 microns or greater. For example, in toothpaste, the particle size is typically in the range of about 10 to 200 microns. Larger particles tend to feel gritty in the mouth and stick between teeth. In many applications, the particle size range is about 40 to 80 microns. The particle sizes can be determined by any of the commonly used methods known in the art such as viewing through a microscope adapted with a calibrated eyepiece.

The containment system of the present invention includes, as a first component, a shell material such as a wax and/or low molecular weight polymer (LWP) which has a softening temperature of about 70° F. or greater. The upper temperature limitation is not critical so long as it is not above the thermal stability or volatility of the oil and/or the core material. For most applications the softening temperature of the shell material is preferably from about 175° to 230° F. The waxes useful in the present invention are natural waxes or synthetic waxes which are well known in the art. Representative examples of such waxes include paraffin wax, carnauba wax, candelilla wax, purified montan wax, castor wax, ceresin wax, bayberry wax, synthetic paraffin waxes, microcrystalline waxes, and polyethylene waxes and blends thereof. Additional waxes having these properties which can be used herein are disclosed in Soap and Chem. Specialties, Volume. 33, page 141 (1957). See also Industrial Waxes, Volume. I and II., H. Band, Chemical Publishing Co., Inc., New York, 1963, for a discussion of waxes and their properties. Representative examples of synthetic low molecular weight polymers include, but are not limited to, poly(1,4-butanediol) bis(4-aminobenzoate), poly(l-butene), poly(1,4-butylene terephthate), polycaprolactone, low density polyethylenes, high density polyethylenes, poly(α-methylstyrene), poly(oxymethylene) acetate end-capped, ethylene-propylene copolymers, polypropylene-graft-maleic anhydride, polystyrene, ethylene vinyl acetate copolymers and blends of the above with waxes. When used in the preparation of food products, the shell material must be FDA approved or on the Generally Recognized As Safe (GRAS) list of safe products for human consumption. The shell material can comprise from about 65 to 95% by weight of the total containment system. Preferably, the shell material is used in concentrations ranging from about 65 to about 75% by weight of the total containment system.

The second component of the containment system is an oil which is compatible with, but not a solvent for the shell material particularly when the shell material is in the solid state. The term oil as used herein refers to oils which are liquids at room temperature and materials which melt and function as oils at the processing temperature. When used in core containment systems in products for human consumption such as toothpaste, chewing gum, and food products, the oil must be FDA approved or on the GRAS list. Examples of oils useful in the present invention include mineral oils; synthetic silicone oils, animal oils such as fish oils, fish-liver oils, sperm oil, omega 3 oils; vegetable oils such as aloe vera, garlic oil, jojoba oil, palm oil, linseed oil, tung oil, octicica oil, soybean oil, cottonseed oil, corn oil, olive oil, safflower oil, castor oil, coconut oil, Vitamin E, etc.; fruit oils such as orange, lime, coconut, cinnamon, cocoa butter; and fragrance/essential oils such as eucalyptus, lavender, lemon and peppermint oil, etc. Low melting point hydrocarbon materials like that of petroleum jelly or red petrolatum or waxes like eicosane, docosane, and other hydrocarbon materials that, at elevated temperatures, change rheology to become oil like in consistency, or blends of the above are useful in the invention. Mineral oil such as Drakeol 35, an FDA approved mineral oil from Penreco, a division of Pennzoil Products, Inc., has been found to be particularly satisfactory.

The amount of oil useful in the present invention is largely dependent upon the type of wax used and the concentration of the wax. It is important that the oil concentration be such that the core material containment system is not tacky so that the particles formed are free-flowing. Typically, the amount of oil in the containment system will be about 30% or less by weight. Preferably the amount of oil will be about 3 to 30% by weight.

In a preferred embodiment of this invention the core material containment system is prepared by a process which comprises the steps of (1) heating a shell material such as a wax or low molecular weight synthetic polymer to a temperature at or above its softening point; (2) adding a sufficient amount of an oil to the molten shell material such that the final core material containment system is not tacky. (3) uniformly dispersing the core material in the molten shell material; (4) cooling the shell material dispersion of core material, while the molten shell material containing the core material is subdivided into individual particles of the desired size, to below the softening temperature of the shell material; and (5) recovering the encapsulated particles.

The shell material is first heated to a temperature above its softening (or melting) point in a vessel equipped with mixing apparatus. The preferred shell materials for the purpose of this process having a softening point within the range from about 175° to about 230° F. It is essential that the shell material be maintained at a temperature above its softening temperature when the core material is added. The maximum temperature is not critical; however, it should not be so high that decomposition occurs or a fire hazard is presented.

The oil and the core material are preferably added to the molten shell material in increments which are sufficiently small to avoid a temperature drop below the softening point of the shell material. Thorough mixing of the core material in the shell material in a molten state is necessary to assure complete dispersion and coating of the core material with the shell material. The containment shell develops as a result of the cooling step.

After uniform dispersion of the oil and core material in the molten shell material has been achieved, the dispersion is cooled to provide individual particles containing the core material encapsulated therein. The individual particles containing the encapsulated materials are obtained by cooling droplets of the molten shell material containing dispersed therein an oil compatible with the molten wax, and a core material. Since cooling is external, it is believed that the shell material solidifies at the surface of the particle and creates a protective barrier or wall for the core material. Preferably, the dispersed particles are solidified by spraying the dispersion into a cool atmosphere which is at a temperature below the softening point of the shell material using a spray gun or other means of obtaining the solid particles. It is important that the particles be at the desired particle size before cooling. Typically, the particle size of the dispersion is varied by changing operational parameters such as viscosity, pressure, temperature and/or the nozzle size settings of the spray gun.

Where a narrow particle size is critical, it may be desirable to screen the particulates to recover the particles of the desired size. Generally, any size particle can be employed depending on the final application of the encapsulated particles. Preferably, the particles are in the size range of about 10 to 200 microns and most preferably about 10 to 100 microns. Size classification in this manner can be accomplished by conventional techniques and equipment such as the double screen Tyler-Hammer Vibrating Sifter.

The preparation of a pigment particle containment system in accordance with the invention is shown by the following example which is presented for the purpose of illustration only, and is not intended to limit the invention.

EXAMPLE 1

10 grams Drakeol 35, an FDA approved mineral oil obtained from Penreco, a division of Pennzoil Products, Inc. and 0.53 grams FD&C blue aluminum # 1 lake (28–31%) obtained from Hilton Davis, Cincinnati, Ohio were added to 23.0 grams molten synthetic paraffin NF wax, a synthetic wax made by the Fisher-Tropsch process and imported by the Koster Keunen Co., Watertown, Conn., with continuous stirring of the molten mixture using a mixer having a propeller type blade. The molten mixture was kept in the molten form by heating on a hot plate kept at a setting to maintain a temperature of about 212–248° F. The molten mixture was continuously stirred for about 2 hours to achieve a good dispersion. The molten mixture was then sprayed into a laboratory adapted cooling box using a laboratory size spray gun available from Binks or DeVilbiss Co. The box was maintained at approximately ambient temperature to provide discrete, non-tacky particles having a particle size in the range of about 40 to 70 microns as determined by viewing through a microscope having a calibrated eyepiece.

EXAMPLE 2

Example 1 was repeated except that it was conducted on a pilot scale using 89,472 grams Drakeol 35 mineral oil and 4,743 grams FD&C blue aluminum #1 lake added to 205,785 grams of molten synthetic paraffin NF wax. The molten wax was sprayed into a pilot scale, stainless steel cooling box equipped with cooling means to maintain the cooling atmosphere at a temperature which is less than the softening temperature of the wax using a commercial Titan Epic model 440E spray gun obtained from Titan Tool, Franklin Lakes, N.J. The recovered particles had an average particle size of about 40 to 70 microns as determined by viewing the particles through a microscope having a calibrated eyepiece.

EXAMPLE 3

Example 1 was repeated using:

| 90 grams | Koster-Keunen synthetic paraffin wax | 60.0% |
|---|---|---|
| 0.75 grams | lemon oil | 0.5% |
| 58.50 grams | mineral oil 35 | 39.0% |
| 0.75 grams | #10 yellow lake | 0.5% |

EXAMPLE 4

Example 1 was repeated using:

| 102.893 grams | Koster-Keunen synthetic paraffin wax | 68.595% |
|---|---|---|
| 2.372 grams | Aluminum lake #10 | 1.581% |
| 15.0 grams | peppermint oil | 10.000% |
| 29.736 grams | mineral oil (Drakeol 35) | 19.824% |

Having described the invention in detail, it will be appreciated that the present specification and claims are provided as means of illustration of the invention and not limitation, and that various modifications and changes may be made without departing from the spirit and scope of the present invention.

What is claimed is:

1. A method for encapsulating or coating a core material with a shell material to provide a core containment system from which leaching of the core material is prevented or controlled, said method comprising the steps of:
   (1) providing a shell material having a softening temperature above about 70° F.;
   (2) heating said shell material to a temperature at or above the softening temperature of said shell material;
   (3) adding an oil to the molten shell material, said oil being compatible with said shell material but not a solvent for the shell material in the solid state;
   (4) uniformly dispersing a core material in the molten, oil-containing shell material;
   (5) subdividing said molten, oil-containing shell material having said core material dispersed therein into individual droplets of a predetermined size by spraying the molten oil-containing shell material having said core material dispersed therein into a cooled atmosphere at a temperature below which the droplets solidify to obtain a plurality of particles of encapsulated or coated core material; and
   (6) recovering said particles of encapsulated or coated core material, wherein said containment system comprises about 65 to 95 wt % shell material, about 3 to 30 wt % oil, and about 0.3 to 3.0 wt % core material.

2. The method of claim 1 wherein said shell material has a softening temperature of about 175 to 230° F. and is a natural wax, a synthetic wax, a low molecular weight synthetic polymer or a blend thereof.

3. The method of claim 2 wherein said shell material is a natural or synthetic wax selected from the group consisting of carnauba wax, candelilla wax, montan wax, castor wax, ceresin wax, bayberry wax, paraffin wax, microcrystaline wax, polyethylene wax, ethylene vinyl acetate and blends thereof.

4. The method of claim 3 wherein said natural or synthetic wax is a paraffin wax.

5. The method of claim 1 wherein said core material comprises a plurality of pigment particles.

6. The method of claim 1 wherein said pigment particles are selected from the group consisting of dyed thermosetting resin particles, chromium oxide pigments, carbon blacks, ultramarine blues, ultramarine pinks, ferric oxides, dyed cellulose particles, and dye lakes.

7. The method of claim 1 wherein said oil is a mineral oil.

8. A core material containment system which prevents or controls leaching of the core material from the containment system, said containment system produced by a method comprising the steps of:
   (1) providing a shell material having a softening temperature above about 70° F.;
   (2) heating said shell material to a temperature at or above the softening temperature of said shell material;
   (3) adding an oil to the molten shell material, said oil being compatible with said shell material but not a solvent for the shell material in the solid state;
   (4) uniformly dispersing a core material in the molten, oil-containing shell material;
   (5) subdividing said molten, oil-containing shell material having said core material dispersed therein into individual droplets of a predetermined size by spraying the molten oil-containing shell material having said core material dispersed therein into a cooled atmosphere at a temperature below which the droplets solidify to obtain a plurality of particles of encapsulated or coated core material; and
   (6) recovering said particles of encapsulated or coated core material, wherein said containment system comprises about 65 to 95 wt % shell material, about 3 to 30 wt % oil, and about 0.3 to 3.0 wt % core material.

9. The system of claim 8 wherein said shell material has a softening temperature of about 175 to 230° F. and is a natural or synthetic wax, a low molecular weight synthetic polymer or a blend thereof.

10. The system of claim 9 wherein said shell material is a natural or synthetic wax selected from the group consisting of candelilla wax, montan wax, castor wax, ceresin wax, bayberry wax, paraffin wax, microcrystalline wax, polyethylene wax, ethylene vinyl acetate, and blends thereof.

11. The system of claim 10 wherein said shell material is a paraffin wax.

12. The system of claim 8 wherein said core material comprises a plurality of pigment particles.

13. The system of claim 10 wherein said pigment particles are selected from the group consisting of dyed thermosetting resin particles, chromium oxide pigments, carbon blacks, ultramarine blues, ultramarine pinks, ferric oxides, dyed cellulose particles, and dye lakes.

14. The system of claim 8 wherein said oil is a mineral oil.

15. A particle containment system which prevents or controls leaching of particles from the particle containment system, said particle containment system comprising about 0.3 to 3.0 wt % particles having a particle size of about 10 to 150 microns; an organic shell material comprising about 65 to 95 wt % natural wax, synthetic wax, low molecular weight synthetic polymer, or a blend thereof, said organic shell material having a softening temperature of about 175 to 230° F.; said organic shell material further containing about 3 to 30 wt % mineral oil, wherein said particles are encapsulated within said mineral oil-containing organic shell material.

16. The system of claim 15 wherein said shell material is a natural or synthetic wax selected from group consisting of carnauba wax, candelilla wax, montan wax, castor wax, ceresin wax, bayberry wax, paraffin wax, microcrystaline wax, polyethylene wax, ethylene vinyl acetate and blends thereof.

17. The system of claim 16 wherein said wax is a paraffin natural or synthetic wax.

18. The system of claim 15 wherein said particles are pigment particles selected from the group consisting of dyed thermosetting resin particles, natural vegetable colors, pigments, dyed cellulose particles, dye lakes, freeze dried particles or spray dried particles, and, optionally, natural or synthetic dyed and/or flavored crystals.

19. The method of claim 1 wherein said system is useful in the preparation of food products and the oil, the shell materials, and the core materials occurs on the Generally Recognized As (GRAS) list.

20. The method of claim 1 wherein the oil is Vitamin E.

21. The system of claim 8 wherein said system is useful in the preparation of food products and the oil, the shell material, and the core material occurs on the Generally Recognized As (GRAS) list.

22. The system of claim 8 wherein the oil is Vitamin E.

* * * * *

UNITED STATES PATENT AND TRADEMARK OFFICE
CERTIFICATE OF CORRECTION

PATENT NO. : 6,060,084
DATED : MAY 9, 2000
INVENTOR(S) : RADMILA SULLIVAN ET AL.

It is certified that error appears in the above-indentified patent and that said Letters Patent is hereby corrected as shown below:

Claim 19, Col. 8, Line 39 - Enter the word --Safe-- before the word "(GRAS)".

Claim 21, Col. 8, Line 44 - Enter the word --Safe-- before the word "(GRAS)".

Signed and Sealed this

Twenty-seventh Day of February, 2001

Attest:

NICHOLAS P. GODICI

Attesting Officer

Acting Director of the United States Patent and Trademark Office